United States Patent
Mohammadi et al.

(10) Patent No.: US 6,649,178 B2
(45) Date of Patent: Nov. 18, 2003

(54) COSMETIC COMPOSITION FOR STRESSED SKIN UNDER EXTREME CONDITIONS

(76) Inventors: Fatemeh Mohammadi, 717 E. Street Hebron, Hebron, CT (US) 06248; Anthony Vargas, 58 Georges La., Monroe, CT (US) 06468

( * ) Notice: Subject to any disclaimer, the term of this patent is extended or adjusted under 35 U.S.C. 154(b) by 0 days.

(21) Appl. No.: 09/880,245

(22) Filed: Jun. 13, 2001

(65) Prior Publication Data

US 2002/0012640 A1 Jan. 31, 2002

Related U.S. Application Data

(60) Provisional application No. 60/211,290, filed on Jun. 13, 2000.

(51) Int. Cl.[7] ............................. A61K 6/00; A61K 7/00; A61K 7/42; A61K 7/44; A61K 7/06
(52) U.S. Cl. .................... 424/401; 424/400; 424/59; 424/60; 424/70.1; 514/844; 514/847
(58) Field of Search ................................ 424/401, 400, 424/70.1, 59, 60; 514/844, 847

(56) References Cited

U.S. PATENT DOCUMENTS

| | | | |
|---|---|---|---|
| 5,306,486 A | * | 4/1994 | McCook et al. .............. 424/59 |
| 5,571,503 A | * | 11/1996 | Mausner |
| 5,716,920 A | * | 2/1998 | Glenn et al. |
| 5,725,874 A | * | 3/1998 | Oda et al. |
| 6,238,678 B1 | * | 5/2001 | Oblong et al. |
| 6,264,995 B1 | * | 7/2001 | Newmark et al. .......... 424/725 |

OTHER PUBLICATIONS

International Search Report dated Nov. 5, 2001 from corresponding PCT application PCT/US01/19200.

PCT Written Opinion dated Jun. 26, 2002 from corresponding PCT application PCT/US01/19200.

* cited by examiner

Primary Examiner—Thurman K. Page
Assistant Examiner—Humera N. Sheikh
(74) Attorney, Agent, or Firm—Herbert Dubno; Jonathan Myers

(57) ABSTRACT

A cosmetic composition is provided effective against stresses of climate extremes. The composition includes hot, cold and dry climate treatment portions. The hot climate treatment portion has a first botanical ingredient to impart a cool sensation, and a sunscreen agent. The cold climate treatment portion has a second botanical ingredient to combat skin inflammation, and a silicone fluid or hydrocarbon for retaining moisturize. The dry climate treatment portion has a third botanical ingredient to impart moisturization and an ester.

1 Claim, No Drawings

COSMETIC COMPOSITION FOR STRESSED SKIN UNDER EXTREME CONDITIONS

This application claims the benefit of U.S. patent application Ser. No. 60/211,290, filed Jun. 13, 2000.

BACKGROUND OF THE INVENTION

1. Field of the Invention

The invention concerns cosmetic compositions for skin subjected to extreme environmental conditions.

2. The Related Art

Humans are often assaulted with uncomfortable climate conditions. Environmental extremes generally induce considerable body discomfort. Hot and humid conditions cause reactions in the skin such as increased expiration through water evaporation. Ultraviolet radiation accompanying the heating phenomena may result in sun damage. Rashes and general erythema may arise from frictional contact with clothing in hot/humid conditions. Dry climate leads to body dehydration. The skin must be re-moisturized. Cold climate also disrupts the skin barrier in a significant way. Cracking and roughness are typical symptoms.

The cosmetic art often addresses these problems in a piecemeal fashion. Healing and protective measures may focus on only one or two problems brought on by climatic conditions.

Accordingly, it is an object of the present invention to provide a cosmetic composition which in a single formulation addresses many of the climatic stresses upon the skin.

It is another object of the present invention to provide a cosmetic composition applicable under a variety of extreme climate conditions to ameliorate effects of heat, cold and dry environmental surroundings.

These and other objects of the present invention will become more readily apparent through consideration of the following summary and detailed description.

SUMMARY OF THE INVENTION

A cosmetic composition is provided for calming skin stressed under a variety of extreme climatic conditions. The composition includes:

(i) from about 0.01 to about 20% of a hot climate treatment portion including:
 (a) a first botanical ingredient imparting a cool sensation present from about 0.1 to about 80% by weight of the hot climate treatment portion;
 (b) an organic sunscreen agent with a chromophoric group active within the ultraviolet radiation range from about 290 to about 400 nm present from about 1 to about 80% by weight of the hot climate treatment portion;

(ii) from about 0.1 to about 95% by weight of a cold climate portion including:
 (a) a second botanical ingredient effective to reduce skin inflammation present from about 0.001 to about 30% by weight of the cold climate treatment portion;
 (b) a silicone fluid or hydrocarbon for retaining moisturize within the skin present from about 1 to about 99% by weight of the cold climate treatment portion;

(iii) from about 0.1 to about 90% by weight of a dry climate treatment portion including:
 (a) a third botanical ingredient to impart moisturization present from about 0.001 to about 10% by weight of the dry climate treatment portion;
 (b) a $C_6$–$C_{40}$ carboxylic ester present from about 1 to about 99% by weight of the dry climate treatment portion.

DETAILED DESCRIPTION OF THE INVENTION

Now it has been found that a single cosmetic formulation can be used against a variety of extreme climate conditions to protect skin. The formulation is based upon pairs of actives each directed at one of three environmental stress conditions including hot, cold and dry climates. A specific type of botanical ingredient is formulated for each of the different climates and to function for different purposes.

The problem of hot climate stress is addressed through a treatment portion present in an amount from about 0.01 to about 20%, preferably from about 1 to about 10% by weight of the cosmetic composition. This treatment portion includes a first botanical ingredient effective to induce a soothing and/or cooling sensation thereby ameliorating effects of hot temperature. Amounts of the first botanical ingredient may range from about 0.1 to about 80%, preferably from about 1 to about 30% by weight of the hot climate treatment portion. Organic sunscreen agents are formulated as a second component to combat sun damage and erythema. These agents are present in amounts from about 1 to about 80%, preferably from about 20 to about 60% by weight of the hot climate treatment portion.

First botanical ingredients suitable for the present invention include trehalose, aloe extract, guava, hydroxy-alpha-sanshool, hydroxy-beta-sanshool, hydroxy-gamma-sanshool, menthol, anethole, isopulegol, menthoxypropane-1,2,diol, menthone, menthyl acetate, eucalyptol, methyl salicylate, N-2,3-trimethyl-2-isopropylbutanamide (available as WS-23 from Wilkinson Sword), N-ethyl-p-menthane-3-carboxamide (available as WS-3 from Wilkinson Sword), menthyl lactate, menthyl succinate, menthone glycerol ketal spilanthol, N-acetyl glycine menthyl ester, L-menthol-3-hydroxybutyrate, 2-isopropenyl-1-methylcyclohexanol, trialkyl-substituted cyclohexane carboxamides, cyclohexanamides, N-ethyl-p-methane-3-carboxamide, 2-mercapto-cyclo-decanone, 2-isopropanyl-5-methylcyclohexanol and mixtures thereof. Particularly preferred are the hydroxy-sanshool compounds which sooth by reducing any hot feeling sensations. These compounds are sold under the Zanthalene trademark from Indena Corporation.

Sunscreen agents for use in the hot climate treatment portion are organic substances having at least one chromophoric group absorbing within the ultraviolet range from about 290 to about 400 nm. Illustrative but not limiting examples include Benzophenone-3 (available as UVINUL M-40), Benzophenone-4 (available as UVINUL MS-40), Benzophenone-8 (available as SPECTRA-SORB UV-24), DEA-Methoxycinnamate (available as BERNEL HYDRO), Ethyl dihydroxypropyl-PABA (available as AMERSCREEN P), Glyceryl PABA (available as NIPA G.M.P.A.), Homosalate (available as KEMESTER HMS), Menthyl anthranilate (available as SUNAROME UVA), Octocrylene (available as UVINUL N-539), Octyl dimethyl PABA (available as AMERSCOL), Octyl methoxycinnamate (avalable as PARSOL MCX), PABA, 2-Phenylbenzimidazole-5-sulphonic acid (available as EUSOLEX 6300), TEA salicylate (available as SUNAROME W), 2-(4-Methoxybenzilidene)-camphor (available as EUSOLEX 6300), Benzophenone-1 (available as UVINUL 400), Benzophenone-2 (available as UVINUL D-50), Benzophenone-6 (available as UVINUL D-49), Benzophenone-12 (available as UVINUL 408), 4-Isopropyl dibenzoyl methane (available as EUSOLEX 8020), Butyl methoxy dibenzoyl methane (available as PARSOL 1789) and Etocrylene (available as UVINUL N-35).

Cold climate treatment portions according to the present invention may range in amount from about 0.1 to about 95%, preferably from about 1 to about 50% by weight of the cosmetic composition. This portion features a second botanical ingredient effective as an anti-irritant to reduce skin inflammation. Amounts of this ingredient may range from about 0.001 to about 30%, preferably from about 0.01 to about 50% by weight of the cold climate treatment portion. A silicone fluid or hydrocarbon is also present for retaining moisture within the skin in amounts which may range from about 1 to about 99%, preferably from about 10 to about 80% by weight of the cold climate treatment portion.

Representative second botanical ingredients include extracts from sea parsley (available from Collaborative Laboratories), red clover, kava kava (available from Sederma Company), watercress, edelweiss, gorgonian extract, oak root extract, cornflower extract, arnica extract, chamomile extract, shikonine, licorice extract (such as glycyrrhetinic acid and salts thereof), absinthium, acacia, escin, alder, buckthorn extract, allantoin, astragalus, astragalus root extract, azulene, baikal skullcap, baizhu, balsam canada, bee pollen, black cohosh, bisabolol, black cohosh extract, blue cohosh, blue cohosh extract, borage, calendula, candula extract, Cangzhu, chickweed, chicory root, chicory root extract, comfrey, comfrey extract, dehurian angelica, devil's claw, dogwood, doggrass, eleuthero, ephedra, evening primrose, eyebright, fang feng, fever few, fisin, forsythia fruit, ganoderma, gaoben, gentian, germanium extract, ginkgo biloba, ginkgo, ginseng extract, golden seal, gotu kola, grape fruit extract, guaiac wood oil, guggal extract, henna, honeysuckle flower, horehound extract, horse chestnut, horse tail, oat extract, peony root, red sage, rosemary, rosmarinic acid, turmeric, yarrow, yeast extract, yucca and mixtures thereof. Most preferred is sea parsley extract.

Hydrocarbons suitable for moisture retention purposes include mineral oil, terpenes (such as squalene and squalane), isoparaffins, polyethylene waxes, and petroleum jelly. Particularly preferred is a microfluidized petrolatum available from Collaborative Laboratories under the trademark of Sansurf Petrolatum-50.

Silicone fluids useful for moisture retention may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms. Linear volatile silicone materials generally have viscosities less than about 5 centistokes at 25° C. while cyclic materials typically have viscosities of less than about 10 centistokes. Examples of commercially available volatile silicone oils are Dow Corning® 344 and Dow Corning® 345.

Nonvolatile silicone oils useful herein include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Silicone copolyols are particularly useful as moisturizing materials within the context of the present invention. Illustrative are Dow Corning® 3225C and 5225C fluids, mixtures of cyclomethicone and dimethicone copolyol having viscosity at 25° C. of 600–2000 cps.

A particularly preferred silicone is marketed under the name of Organza™, available from DIOW Products, Inc., Green Lawn, N.Y. Organza™ is a combination of polyethylene, dimethylsiloxane, phenyltrimethicone, dimethicone copolyol and cyclomethicone.

Crosslinked non-emulsifying polysiloxane elastomers may also be useful for the present invention. By the term "non-emulsifying" is meant the absence of polyoxyalkylene groups. Advantageously the elastomers are formed from a divinyl compound, particularly a polymer with at least two free vinyl groups, reacting with Si–H linkages of a polysiloxane backbone such as a molecularly spherical MQ resin. Commercially elastomers are available from a variety of sources including the General Electric Company, Dow Corning and Shin Etsu Chemical Companies. Assigned INCI names for these materials are Cyclomethicone, Dimethicone/Vinyl Dimethicone Crosspolymer, Dimethicone Dimethicone/Vinyl Dimethicone Crosspolymer, Cyclomethicone Dimethicone/Vinyl Dimethicone Crosspolymer, Phenyl Trimethicone Dimethicone/Phenyl Vinyl Dimethicone Crosspolymer and Crosslinked Stearyl Methyl Dimethyl Siloxane Copolymer.

Cosmetic compositions of the present invention will also contain a dry climate treatment portion. Amounts of this portion may range from about 0.1 to about 90%, preferably from about 1 to about 50% by weight of the cosmetic composition. Included within the dry climate treatment portion is a third botanical ingredient effective for imparting moisturization. Amounts of this ingredient may range from about 0.001 to about 10%, preferably from about 1 to about 5% by weight of the dry climate treatment portion. Additionally, this portion includes an ester and/or hydrocarbon emollient present in amount from about 1 to about 99%, preferably from about 10 to about 70% by weight of the dry climate treatment portion.

Representatives of the third botanical ingredient include extracts of sea pine, prickly pears, orotic acid, hydrolyzed casein, hydrolyzed collagen, hydrolyzed conchorin protein, hydrolyzed corn protein, hydrolyzed elastin, hydrolyzed potato protein, hydrolyzed rice protein, hydrolyzed silk, hydrolyzed soy protein, hydrolyzed wheat protein, phytoglycolipid, millet extract, sigmasterol, sitosterol, soybean sterols, canola derived sterols, campesterol, brassicasterol and combinations thereof.

Esters, hydrocarbons and combinations thereof are useful for their occlusive properties combating dry climate conditions. Esters are $C_6$–$C_{40}$ carboxylic substances such as:

(1) Alkenyl or alkyl esters of fatty acids having 10 to 20 carbon atoms. Examples thereof include isoarachidyl neopentanoate, isononyl isononanoate, oleyl myristate, oleyl stearate, octyl stearate and oleyl oleate.

(2) Ether-esters such as fatty acid esters of ethoxylated fatty alcohols.

(3) Polyhydric alcohol ester. Ethylene glycol mono and di-fatty acid esters, diethylene glycol mono- and di-fatty acid esters, polyethylene glycol (200–6000) mono- and di-fatty acid esters, propylene glycol mono and di-fatty acid ester, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Mono-, Di- and Triglyceride esters such as PEG-8 caprylic/capric triglyceride.

(5) Sterols esters, of which cholesterol fatty acid esters are examples thereof.

Particularly preferred esters are bean tree oil (mostly capryl isostearate), alkyl fumarates such as di-$C_{12}$–$C_{15}$ alkyl fumarates and shea butter available as alpha-Amerin.

Optionally the cosmetic compositions may include a humid climate treatment portion for imparting a powdery feel. Amounts of this portion may range from about 0.1 to about 80% by weight of the cosmetic composition. The humid climate portion will include from about 0.001 to about 10% by weight of that portion of an impalpable powder. Illustrative powders include polyethylene, polyamides, boron nitrides, clays, quaternary ammonium, organo-modified clays and mixtures thereof.

Compositions of the present invention may include thickeners and gelling agents. Particularly suitable for such purpose are acrylic acid/ethyl acrylic copolymers and the carboxyvinyl polymers sold by the B.F. Goodrich Company under the trademark of Carbopol resins. These resins consist essentially of a colloidally water-soluble polyalkenyl polyether polymer of acrylic acid cross-linked with from 0.75 to 2.00% of a cross-linking agent such as, for example, polyallyl sucrose or polyallyl pentaerythritol. Examples include Carbopol 945, Carbopol 940, Carbopol 950, Carbopol 954, Carbopol 980, Carbopol 951 and Carbopol 981. Also suitable for use herein are hydrophobically-modified cross-linked polymers of acrylic acid having amphipathic properties available under the trademark Carbopol 1382, Carbopol 1342 and Pemulen TR-1 (CTFA Designation: Acrylates/ 10–30 Alkyl Acrylate Crosspolymer). Carbopol 1382 is a water-soluble polymer of acrylic acid cross-linked with about 1% of a polyallyl ether of sucrose having an average of about 5.8 allyl groups for each sucrose molecule. A combination of the polyalkenyl polyether cross-linked acrylic acid polymer and the hydrophobically modified cross-linked acrylic acid polymer is also suitable. Amounts of the polymer may range from about 0.1 to about 10%, preferably from about 0.05 to about 3%, optimally from about 0.1 to about 1% by weight of the cosmetic composition.

Humectants may also be incorporated into the cosmetic compositions. Humectants are polyhydric alcohols which typically include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Most preferably the humectant is glycerin. Amounts of humectant may range anywhere from about 0.1 to about 50%, preferably from about 0.5 to about 20%, optimally from about 1 to about 3% by weight of the cosmetic composition.

Water may be present as a carrier in amounts ranging from about 1 to about 99%, preferably from about 20 to about 70%, optimally from about 30 to about 50% by weight of the cosmetic composition. Especially useful are emulsions which may be of the oil-in-water, water-in-oil or duplex variety. Most especially, the invention is concerned with the water-in-oil variety. Aqueous to oily phases may range in weight from about 10:1 to about 1:10, preferably from about 1:1 to about 2:1, optimally from about 1:1 to about 1.5:1.

Emulsifiers may be a further component of compositions according to the present invention. These may be selected from nonionic, anionic, cationic or amphoteric emulsifying agents. They may range in amount anywhere from about 0.1 to about 20% by weight of the cosmetic composition. Illustrative nonionic emulsifiers are alkoxylated compounds based on $C_{10}$–$C_{22}$ fatty alcohols and acids, and sorbitan. These materials are available, for instance, from the Shell Chemical Company under the Neodol trademark. Copolymers of polyoxypropylene-polyoxyethylene, sold by the BASF Corporation under the Pluronic trademark are sometimes useful. Alkyl polyglycosides available from the Henkel Corporation may also be utilized for purposes of this invention. Most preferred as nonionic emulsifiers are steareth-2, steareth-21 and especially mixtures thereof in ratios of 10:1 to 1:10.

Anionic type emulsifiers include fatty acid soaps, sodium lauryl sulphates, sodium lauryl ether sulphates, alkyl benzene sulphonates, sarcosinates, taurates, mono- and di-alkyl acid phosphates and fatty acyl isethionates.

Amphoteric emulsifiers include such materials as dialkylamine oxide and various types of betaines (such as cocamidopropyl betaine).

Preservatives can desirably be incorporated into the compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the present compositions. Suitable traditional preservatives are alkyl esters of parahydroxybenzoic acid. Other preservatives which have more recently come into use include hydantoin derivatives, propionate salts and a variety of quaternary ammonium compounds. Cosmetic chemists are familiar with appropriate preservatives and routinely choose them to satisfy the preservative challenge test and to provide product stability. Particularly preferred preservatives are methyl paraben, propyl paraben, imidazolidinyl urea, sodium dehydroacetate, phenoxyethanol and benzyl alcohol. The preservatives should be selected having regard for the use of the composition and possible incompatibilities between the preservatives and other ingredients. Preservatives are preferably employed in amounts ranging from 0.01% to 2% by weight of the cosmetic composition.

Minor adjunct ingredients may also be included such as fragrances, antifoam agents, opacifiers and colorants, each in their effective amounts to accomplish their respective functions.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLES 1–8

Cosmetic compositions according to the present invention are typified by the formulations described under Table I.

TABLE I

| INGREDIENT | \multicolumn{8}{c}{EXAMPLE (WEIGHT %)} |
|---|---|---|---|---|---|---|---|---|

| INGREDIENT | 1 | 2 | 3 | 4 | 5 | 6 | 7 | 8 |
|---|---|---|---|---|---|---|---|---|
| PHASE A | | | | | | | | |
| Aloe Vera Gel | 0.50 | 0.50 | 0.50 | 0.50 | 0.50 | 0.50 | 0.50 | 0.50 |
| Carbopol 1382 ® (2% Active in Water) | 20.00 | 20.00 | 20.00 | 20.00 | 20.00 | 20.00 | 20.00 | 20.00 |
| Disodium EDTA | 0.10 | 0.10 | 0.10 | 0.10 | 0.10 | 0.10 | 0.10 | 0.10 |
| Butylene Glycol | 1.00 | 1.00 | 1.00 | 1.00 | 1.00 | 1.00 | 1.00 | 1.00 |
| Glycerin | 1.50 | 1.50 | 1.50 | 1.50 | 1.50 | 1.50 | 1.50 | 1.50 |
| Allantoin | 0.09 | 0.09 | 0.09 | 0.09 | 0.09 | 0.09 | 0.09 | 0.09 |
| Deionized Water | Bal. | Bal. | Bal. | Bal. | Bal. | Bal. | Bal. | Bal. |
| PHASE B | | | | | | | | |
| Shea Butter | 2.00 | 2.00 | 2.00 | 2.00 | 2.00 | 2.00 | 2.00 | 2.00 |
| Di $C_{12}$–$C_{15}$ Alkyl Fumarate | 1.00 | 1.00 | 1.00 | 1.00 | 1.00 | 1.00 | 1.00 | 1.00 |
| Butyloctyl Salicylate | 3.00 | 3.00 | 3.00 | 3.00 | 3.00 | 3.00 | 3.00 | 3.00 |
| Parsol MCX ® | 4.00 | 4.00 | 4.00 | 4.00 | 4.00 | 4.00 | 4.00 | 4.00 |
| Benzophenone-3 | 3.00 | 3.00 | 3.00 | 3.00 | 3.00 | 3.00 | 3.00 | 3.00 |
| Parsol 1789 ® | 2.00 | 2.00 | 2.00 | 2.00 | 2.00 | 2.00 | 2.00 | 2.00 |
| Super Sterol Ester | 0.80 | 0.80 | 0.80 | 0.80 | 0.80 | 0.80 | 0.80 | 0.80 |
| Stearyl Alcohol | 1.20 | 1.20 | 1.20 | 1.20 | 1.20 | 1.20 | 1.20 | 1.20 |
| Steareth-2 | 2.62 | 2.62 | 2.62 | 2.62 | 2.62 | 2.62 | 2.62 | 2.62 |
| Steareth-21 | 0.87 | 0.87 | 0.87 | 0.87 | 0.87 | 0.87 | 0.87 | 0.87 |
| Bean Tree Oil | 4.00 | 4.00 | 4.00 | 4.00 | 4.00 | 4.00 | 4.00 | 4.00 |
| Phenonip | 0.58 | 0.58 | 0.58 | 0.58 | 0.58 | 0.58 | 0.58 | 0.58 |
| PHASE C | | | | | | | | |
| Vitamin E Acetate | 0.20 | 0.20 | 0.20 | 0.20 | 0.20 | 0.20 | 0.20 | 0.20 |
| Silicone DC 200 Fluid (6cST) | 3.00 | 3.00 | 3.00 | 3.00 | 3.00 | 3.00 | 3.00 | 3.00 |
| Organza* | 4.00 | 3.00 | 2.00 | 1.00 | 0.50 | 5.00 | 6.00 | 10.00 |
| Siloxane Elastomer (Shin Etsu KSG-15 ®) | 2.00 | 2.00 | 2.00 | 2.00 | 2.00 | 2.00 | 2.00 | 2.00 |
| PHASE D | | | | | | | | |
| Deionized Water | 1.83 | 1.83 | 1.83 | 1.83 | 1.83 | 1.83 | 1.83 | 1.83 |
| Triethanolamine | 0.90 | 0.90 | 0.90 | 0.90 | 0.90 | 0.90 | 0.90 | 0.90 |
| DL-Panthanol | 0.20 | 0.20 | 0.20 | 0.20 | 0.20 | 0.20 | 0.20 | 0.20 |
| PHASE E | | | | | | | | |
| Advanced Moisture Complex** | 1.00 | 1.00 | 1.00 | 1.00 | 1.00 | 1.00 | 1.00 | 1.00 |
| Sea Parsley Extract | 0.01 | 0.01 | 0.01 | 0.01 | 0.01 | 0.01 | 0.01 | 0.01 |
| Red Clover Extract | 2.00 | 2.00 | 2.00 | 2.00 | 2.00 | 2.00 | 2.00 | 2.00 |
| Kava Kava | 0.50 | 0.50 | 0.5 | 0.50 | 0.50 | 0.50 | 0.50 | 0.50 |
| Phenoxyethanol | 0.40 | 0.40 | 0.40 | 0.40 | 0.40 | 0.40 | 0.40 | 0.40 |
| Sansurf ® Petrolatum-50 | 7.00 | 7.00 | 7.00 | 7.00 | 7.00 | 7.00 | 7.00 | 7.00 |
| Botanical Blend*** | 2.00 | 2.00 | 2.00 | 2.00 | 2.00 | 2.00 | 2.00 | 2.00 |

*Mixture of polyethylene, dimethyl siloxane, phenyl trimethicone and dimethicone copolyol in cyclomethicone
**Mixture of sodium hyaluronate, sodium PCA, urea, Polyquaternium-51, glycerin, trehalose and water.
***Blend of Bitter Sweet, Guava, Sea Pine, Prickly Pear, Edelweiss and watercress.

The foregoing description and examples illustrate selected embodiments of the present invention. In light thereof variations and modifications will be suggested to one skilled in the art, all of which are within the spirit and purview of this invention.

What is claimed is:

1. A cosmetic composition for calming skin stressed under a variety of extreme climate conditions consisting essentially of a mixture of aloe vera gel, sea parsley extract, red clover extract, kava kava extract, bittersweet extract, guava extract, sea pine extract, prickly pear extract, edelweiss extract and watercress extract as active botanical ingredients together with an organic sun screen agent with a chromophoric group active within the ultraviolet radiation range from about 290 nm to about 400 nm, a silicone fluid or hydrocarbon for retaining moisture within the skin, and a $C_6$ to $C_{40}$ carboxylic ester.

* * * * *